(12) United States Patent
Arnone

(10) Patent No.: US 12,097,119 B2
(45) Date of Patent: Sep. 24, 2024

(54) INTERBODY SPACER FOR SPINAL FUSION

(71) Applicant: CORELINK, LLC, St. Louis, MO (US)

(72) Inventor: Josh Arnone, St. Charles, MO (US)

(73) Assignee: CORELINK, LLC, St. Louis, MO (US)

( * ) Notice: Subject to any disclaimer, the term of this patent is extended or adjusted under 35 U.S.C. 154(b) by 309 days.

(21) Appl. No.: 17/664,150

(22) Filed: May 19, 2022

(65) Prior Publication Data

US 2022/0346958 A1 Nov. 3, 2022

Related U.S. Application Data

(63) Continuation of application No. 16/722,090, filed on Dec. 20, 2019, now Pat. No. 11,357,632, which is a continuation of application No. 15/792,140, filed on Oct. 24, 2017, now Pat. No. 10,512,545.

(60) Provisional application No. 62/412,091, filed on Oct. 24, 2016.

(51) Int. Cl.
*A61F 2/30* (2006.01)
*A61F 2/44* (2006.01)
*A61F 2/28* (2006.01)
*A61F 2/46* (2006.01)

(52) U.S. Cl.
CPC ...... *A61F 2/30767* (2013.01); *A61F 2/30771* (2013.01); *A61F 2/30907* (2013.01); *A61F 2/4455* (2013.01); *A61F 2/4465* (2013.01); *A61F 2/447* (2013.01); *A61F 2002/2835* (2013.01); *A61F 2002/30011* (2013.01); *A61F 2002/30774* (2013.01); *A61F 2002/30904* (2013.01); *A61F 2002/3092* (2013.01); *A61F 2002/3093* (2013.01); *A61F 2002/30968* (2013.01); *A61F 2002/30978* (2013.01); *A61F 2002/30985* (2013.01); *A61F 2002/4629* (2013.01)

(58) Field of Classification Search
CPC .................................................. A61F 2/30767
See application file for complete search history.

(56) References Cited

U.S. PATENT DOCUMENTS

| | | | | |
|---|---|---|---|---|
| 4,834,757 A | * | 5/1989 | Brantigan | A61F 2/42 623/17.11 |
| 4,863,476 A | * | 9/1989 | Shepperd | A61F 2/4455 623/17.15 |
| 5,171,278 A | * | 12/1992 | Pisharodi | A61F 2/446 606/279 |
| 5,282,861 A | * | 2/1994 | Kaplan | B22F 3/114 623/23.51 |

(Continued)

FOREIGN PATENT DOCUMENTS

| | | |
|---|---|---|
| CN | 105559950 A | 5/2016 |
| WO | 2017191223 A1 | 11/2017 |

*Primary Examiner* — Christian A Sevilla
(74) *Attorney, Agent, or Firm* — Stinson LLP

(57) ABSTRACT

An interbody spacer for spinal fusion surgery includes first and second opposite side walls that have open-cell metal foam at upper and lower faces, and a three-dimensional lattice disposed between open-cell metal foam at the upper and lower faces. The open-cell metal foam is in communication with the three-dimensional lattice so that bone growth can enter the three-dimensional lattice from the open-cell metal foam. The interbody spacer may be formed by additive manufacturing.

13 Claims, 16 Drawing Sheets

(56) References Cited

U.S. PATENT DOCUMENTS

| | | | |
|---|---|---|---|
| 5,702,449 A * | 12/1997 | McKay | A61L 27/44 623/17.16 |
| 2003/0009227 A1 | 1/2003 | Lambrecht | |
| 2003/0040802 A1 | 2/2003 | Errico | |
| 2003/0065396 A1 | 4/2003 | Michelson | |
| 2003/0105527 A1 | 6/2003 | Bresina | |
| 2003/0109933 A1 | 6/2003 | Weissman | |
| 2003/0135276 A1* | 7/2003 | Eckman | A61F 2/4611 623/17.11 |
| 2003/0153985 A1 | 8/2003 | Lee | |
| 2003/0158553 A1 | 8/2003 | Michelson | |
| 2004/0019386 A1 | 1/2004 | Ferree | |
| 2004/0034351 A1 | 2/2004 | Sherman | |
| 2004/0059418 A1 | 3/2004 | McKay | |
| 2005/0112397 A1 | 5/2005 | Rolfe | |
| 2006/0241765 A1 | 10/2006 | Burn | |
| 2006/0241776 A1 | 10/2006 | Brown | |
| 2007/0118229 A1 | 5/2007 | Bergin | |
| 2007/0198021 A1 | 8/2007 | Wales | |
| 2007/0219634 A1 | 9/2007 | Greenhalgh | |
| 2008/0077247 A1 | 3/2008 | Murillo | |
| 2008/0124766 A1 | 5/2008 | Kuboki | |
| 2009/0048675 A1 | 2/2009 | Bhatnagar et al. | |
| 2010/0198353 A1 | 8/2010 | Pope | |
| 2011/0125284 A1 | 5/2011 | Gabbrielli et al. | |
| 2012/0316650 A1 | 12/2012 | Ullrich, Jr. et al. | |
| 2013/0030529 A1 | 1/2013 | Hunt | |
| 2014/0107786 A1 | 4/2014 | Geisler et al. | |
| 2015/0018956 A1 | 1/2015 | Steinmann et al. | |
| 2016/0158023 A1 | 6/2016 | Klimek | |
| 2017/0173225 A1 | 6/2017 | Troxel | |
| 2017/0266007 A1 | 9/2017 | Gelaude et al. | |
| 2018/0110624 A1 | 4/2018 | Arnone | |
| 2018/0289496 A1 | 10/2018 | Zappacosta et al. | |
| 2018/0338838 A1 | 11/2018 | Cryder et al. | |
| 2019/0038428 A1* | 2/2019 | Stauffer | A61F 2/30771 |
| 2019/0053907 A1 | 2/2019 | Gregersen et al. | |
| 2019/0083270 A1 | 3/2019 | Milz et al. | |
| 2019/0142601 A1* | 5/2019 | Ashleigh | A61F 2/447 623/17.16 |
| 2019/0175354 A1 | 6/2019 | Knox et al. | |
| 2019/0224023 A1 | 7/2019 | Howard et al. | |

\* cited by examiner

INTERBODY SPACER FOR SPINAL FUSION

STATEMENT OF RELATED CASES

This application is a continuation of U.S. Non-Provisional application Ser. No. 16/722,090, filed Dec. 20, 2019, which claim is a continuation of U.S. Non-Provisional application Ser. No. 15/792,140, filed Oct. 24, 2017, Issued as U.S. Ser. No. 10/512,545 on Dec. 24, 2019, which claims the benefit of U.S. Provisional Application No. 62/412,091, filed Oct. 24, 2016, the entire contents of each of which are incorporated herein by reference.

FIELD OF THE DISCLOSURE

The present disclosure generally relates to an interbody spacer for spinal fusion.

BACKGROUND OF THE DISCLOSURE

Spinal fusion is a surgical procedure used to correct problems with vertebrae of the spine. Spinal fusion fuses together the painful vertebrae so that they heal into a single, solid bone. In one method, the intervertebral disc between two vertebrae is removed and a small interbody spacer, also known as a cage, is inserted between the vertebrae. These interbody spacers usually contain bone graft material to promote bone healing and facilitate the fusion. After the interbody spacer is inserted, surgeons often use metal screws, plates, and rods to further stabilize the spine. Two common spinal fusion procedures are posterior lumbar interbody fusion (PLIF) and transforaminal lumbar interbody fusion (TLIF). The type of interbody spacer is dependent on the type of fusion procedure being performed.

SUMMARY

In one aspect, an interbody spacer for spinal fusion surgery generally comprises first and second opposite longitudinal end portions. A longitudinal axis of the interbody spacer extends through the first and second opposite end portions. First and second opposite side walls extend longitudinally between and interconnect the first and second longitudinal end portions. The first and second opposite side walls define a width of the interbody spacer therebetween. Upper and lower faces are at respective upper and lower portions of the corresponding first and second opposite longitudinal end portions and first and second opposite side walls. The upper and lower faces define a height of the interbody spacer therebetween. An interior cavity is defined by the first and second opposite longitudinal end portions and the first and second opposite side walls. The interior cavity extends through the upper and lower faces. Each of the first and second opposite side walls includes open-cell metal foam at the upper and lower faces, and a three-dimensional lattice disposed between the open-cell metal foam at the upper and lower faces. The open-cell metal foam is in communication with the three-dimensional lattice so that bone growth can enter the three-dimensional lattice from the open-cell metal foam.

In another aspect, a method of forming the interbody spacer set forth above generally comprises forming the interbody spacer as a monolithic, one-piece component by additive manufacturing process.

BRIEF DESCRIPTION OF THE DRAWINGS

Corresponding reference characters indicate corresponding parts throughout the drawings.

DETAILED DESCRIPTION OF THE DISCLOSURE

As used herein, "open-cell metal foam" is a porous structural component having a relatively roughened surface, an apparent randomized filament arrangement, and cell sizes and shapes forming an interconnected network or labyrinth to facilitate bone in-growth.

As used herein, a "three-dimensional lattice" is a porous structural component including non-randomized, intersecting struts forming patterns of interconnected passages to facilitate bone growth.

Figure 1:
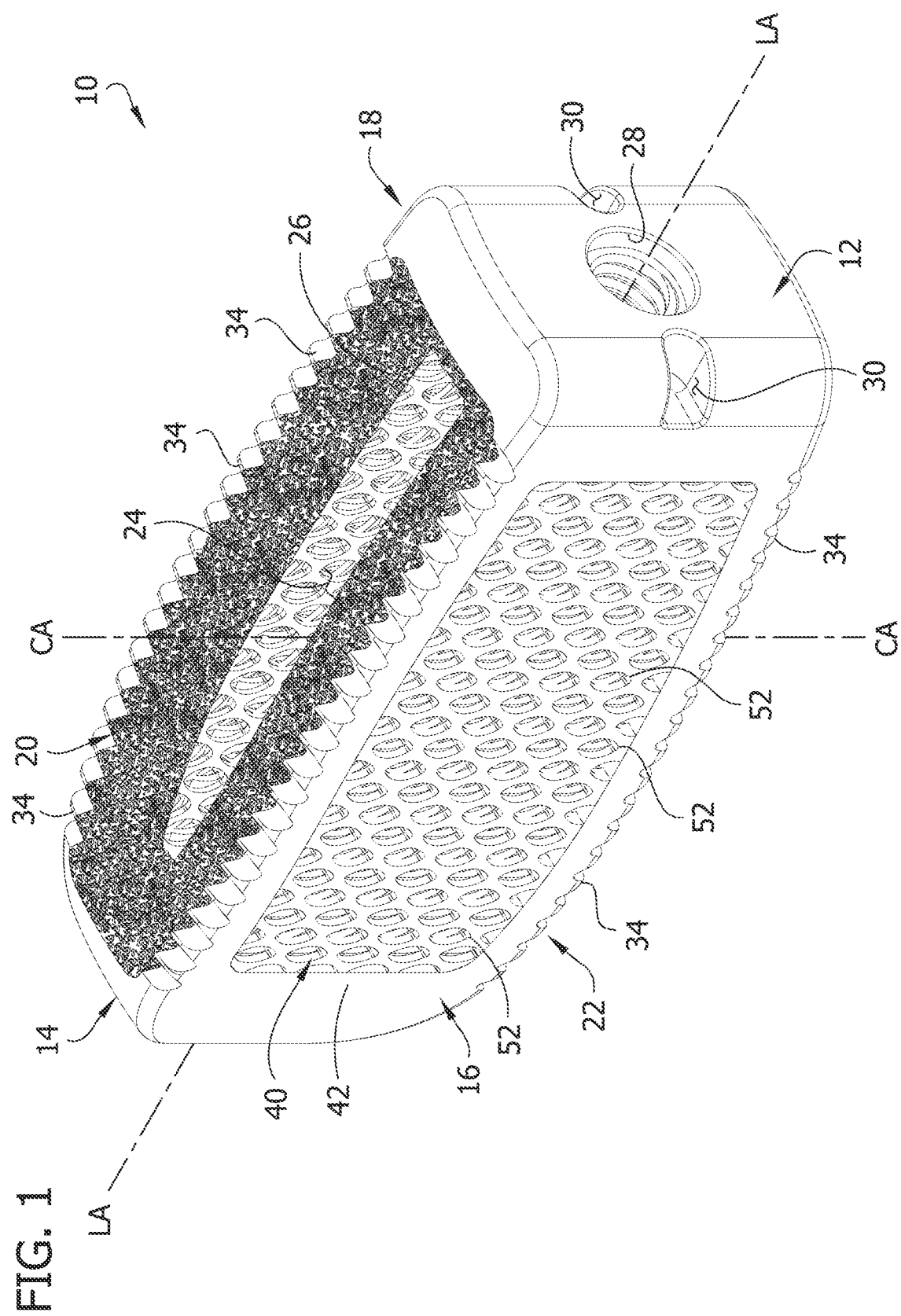
FIG. 1 is a perspective of one embodiment of an interbody spacer constructed according to the teachings of the present disclosure.
Figure 2:
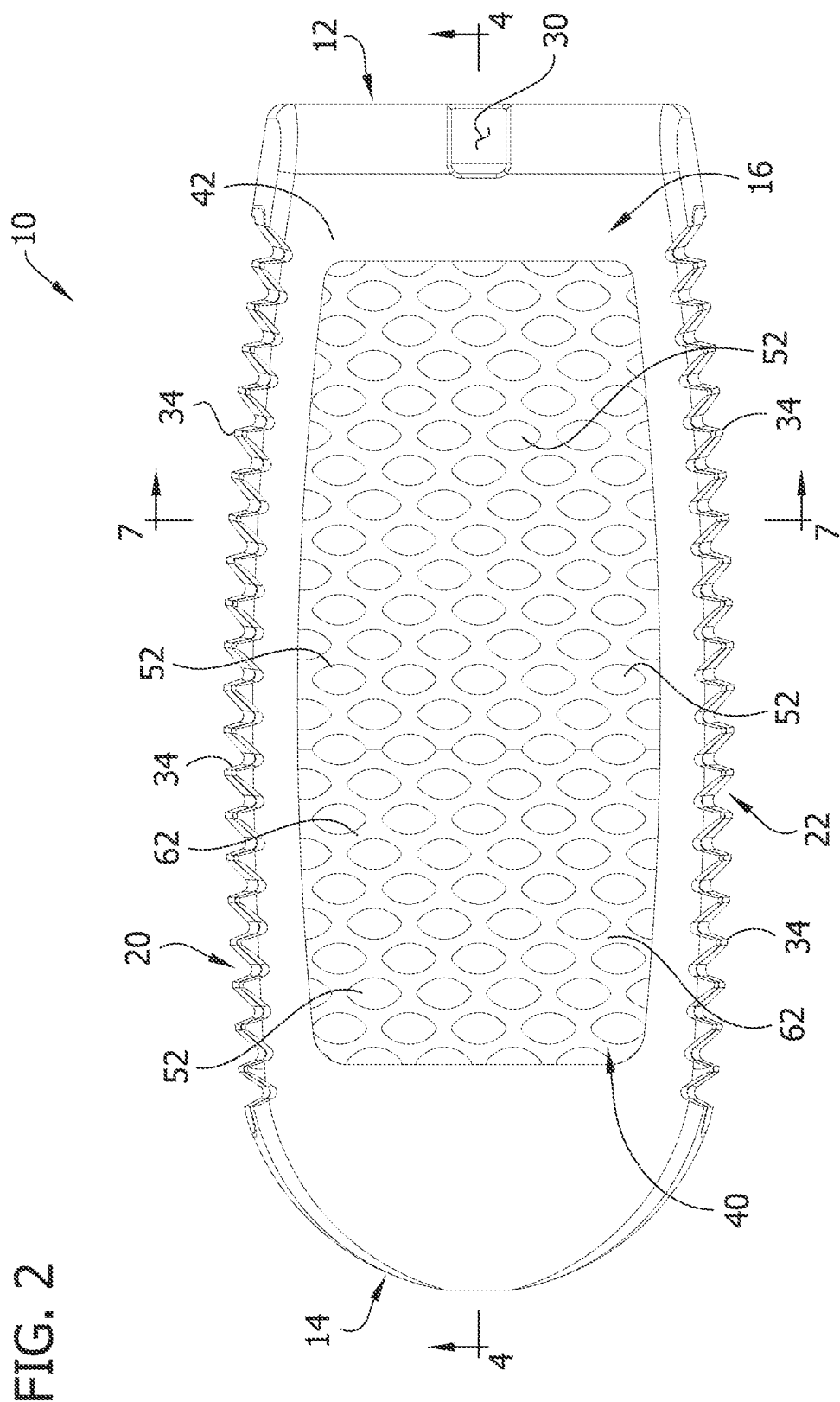
FIG. 2 is a side elevation of the interbody spacer of FIG. 1.

Referring to FIG. 1 of the drawings, a first embodiment of an interbody spacer is generally indicated at reference numeral 10. This interbody spacer 10 is designed for use in posterior lumbar interbody fusion (PLIF) surgery, and is referred to as a PLIF interbody spacer. The PLIF spacer 10 includes a longitudinal axis LA extending through opposite first and second longitudinal end portions, generally indicated at 12, 14 (i.e., proximal and distal longitudinal ends); opposing first and second side walls, generally indicated at 16, 18 extending longitudinally between the first and second longitudinal ends and defining a transverse dimension (e.g., width) of the interbody spacer therebetween; and opposite upper and lower faces, generally indicated at 20, 22, defining height of the interbody spacer therebetween. Interior surfaces of the first and second side walls and the first and second longitudinal end portions define a large, interior cavity 24 extending heightwise through the upper and lower faces generally transverse to the longitudinal axis. The interior cavity 24 is configured to receive bone graft material to facilitate bone growth. As used herein, terms such as "inner," "outer," "inward," "outward," "exterior," and "interior," relate to locations relative to the interior cavity.

The first and second longitudinal end portions 12, 14 comprise generally solid bodies (e.g., titanium or other metal or other material) to enhance the structurally integrity (e.g., compressive strength) of the spacer at the longitudinal end portions. The illustrated first and second longitudinal end portions 12, 14 also comprise open-cell metal foam 26 (e.g., titanium or other metal) on the interior surface of the solid bodies and partially defining the interior cavity 24 to enhance bone growth. The open-cell metal foam 26 extends along the entire heights and widths of the interior surfaces of the longitudinal end portions 12, 14 (i.e., the open-cell metal foam covers entireties of the interior surfaces of the longitudinal end portions). It is understood that the longitudinal end portions 12, 14 may not include the open-cell metal foam 26 and may be of other constructions. The first longitudinal end portion 12 defines a tool-receiving opening 28 extending longitudinally from an exterior of the interbody spacer 10. The tool-receiving opening 28, which may be threaded as illustrated, is configured to receive a suitable insertion tool for use in inserting the interbody spacer 10 in the patient. Tool-receiving grooves 30 are formed in the first longitudinal end portion 12 on opposite sides of the tool-receiving opening 28 for receiving jaws of a suitable insertion tool. The interbody spacer 10 may include other features for use with a suitable insertion tool. The second longitudinal end 14 portion has a bullet-nose shape to facilitate insertion of the interbody spacer 10 in the patient. The second longitudinal end portion 14 may be of other configurations.

The first and second side walls 16, 18 include rows of teeth 34 at the upper and lower faces 20, 22. The rows of teeth 34 extend longitudinally adjacent the outer margins (i.e., outer perimeter) of the upper and lower faces 22, 24 relative to the central axis of the interior cavity 24. That is, the first and second side walls 16, 18 are serrated at the upper and lower faces 22, 24 adjacent the outer margins of the upper and lower faces. Each tooth 34 extends in a direction generally toward the first longitudinal end 12. The rows of teeth 34 facilitate anchoring of the interbody spacer 10 to the adjacent vertebrae within the interbody space to inhibit movement of the interbody spacer within the space. In other embodiments, the interbody spacer 10 may include other features to facilitate anchoring and inhibit movement of the interbody spacer within interbody space.

Figure 3:
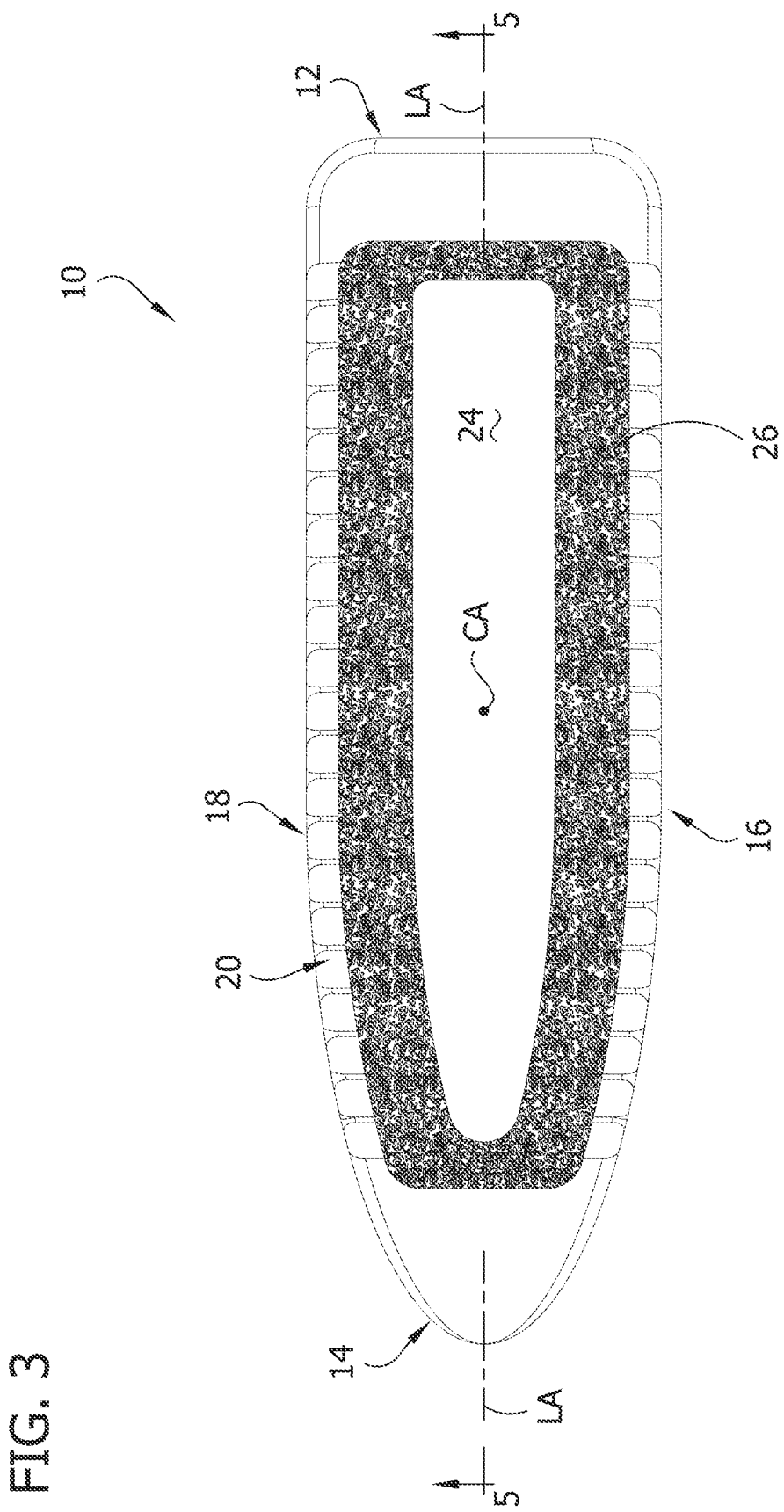
FIG. 3 is a top plan view of the interbody spacer of FIG. 1.
Figure 7:
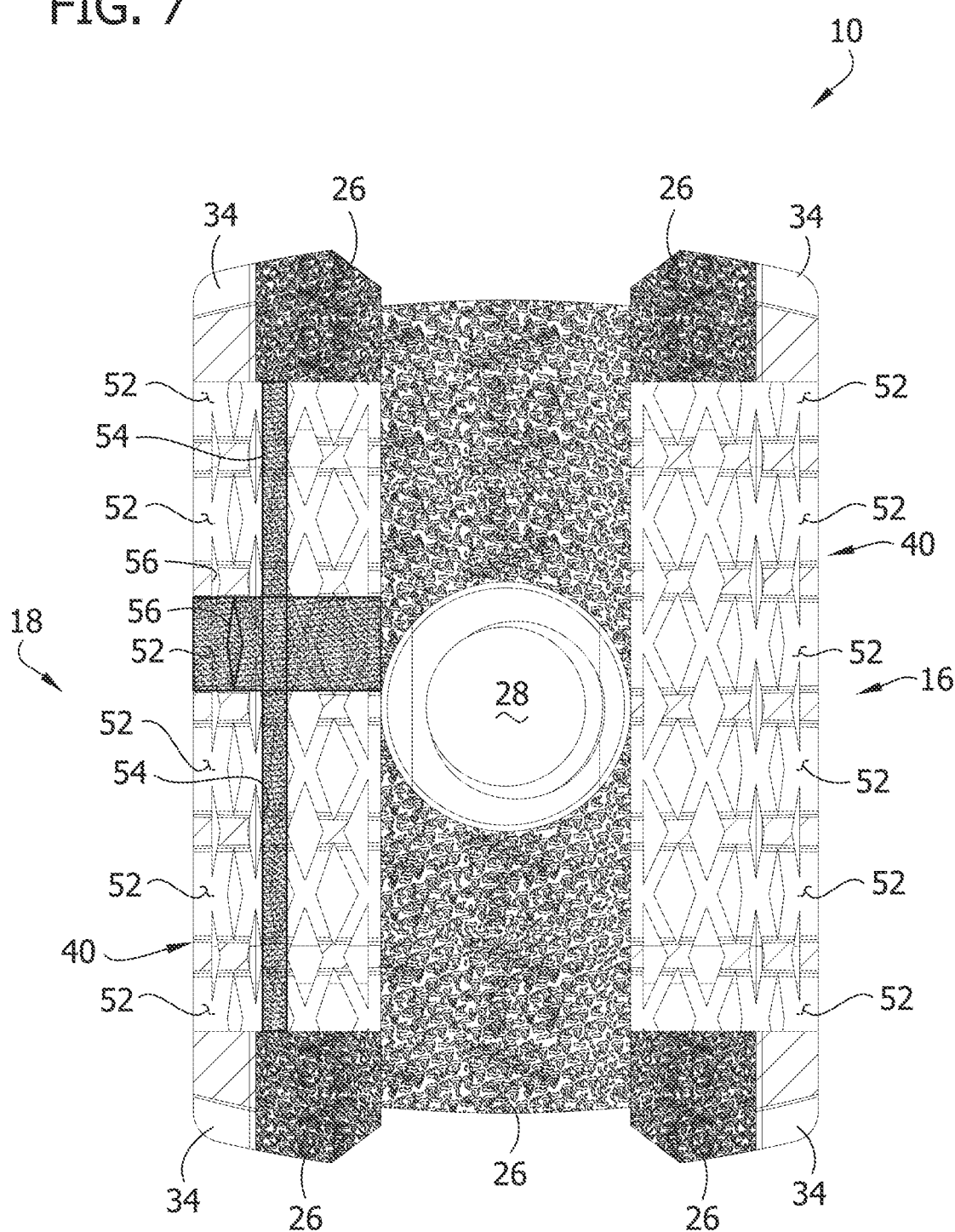
FIG. 7 is a cross section of the interbody spacer taken in the plane defined by the line 7-7 in FIG. 2.

As shown in FIGS. 3 and 7, the first and second side walls 16, 18 also include open-cell metal foam 26 at the upper and lower faces 20, 22 and disposed inward of the corresponding rows of teeth 34 (e.g., serrations). Together with the longitudinal end portions 12, 14, open-cell metal foam 26 surrounds upper and lower edge margins of the interior cavity 24. The open-cell metal foam 26 of the first and second side walls 16, 18 has a depth less than the entire heights of the first and second side walls. In other words, as shown in FIG. 7, the open-cell metal foam 26 of the first and second side walls 16, 18 extends only partially along the heights of the respective first and second side walls from the corresponding upper and lower faces 20, 22 of the interbody spacer 10. Overall, the open-cell metal foam 26 of the first and second side walls 16, 18 has a width extending inward and a depth extending either from the upper face 20 toward the lower face 22 or from the lower face toward the upper face. Exposed surfaces of the open-cell metal foam 26 at the upper and lower faces 20, 22 are generally rough. To inhibit the open-cell metal foam 26 from snagging on tissue, such as a nerve, during insertion of the PLIF interbody spacer 10 during surgery, recessed portions of the open-cell metal foam adjacent the teeth 34 are smooth (i.e., smoother) relative to the remaining portions of the open-cell metal foam and recessed in a heigthwise direction relative to the teeth such that the teeth extend beyond the recessed portions in the heightwise direction. The remaining portions of the open-cell metal foam 26 inward of the recessed portions may extend beyond the teeth 34 in the heightwise direction.

Figure 4:
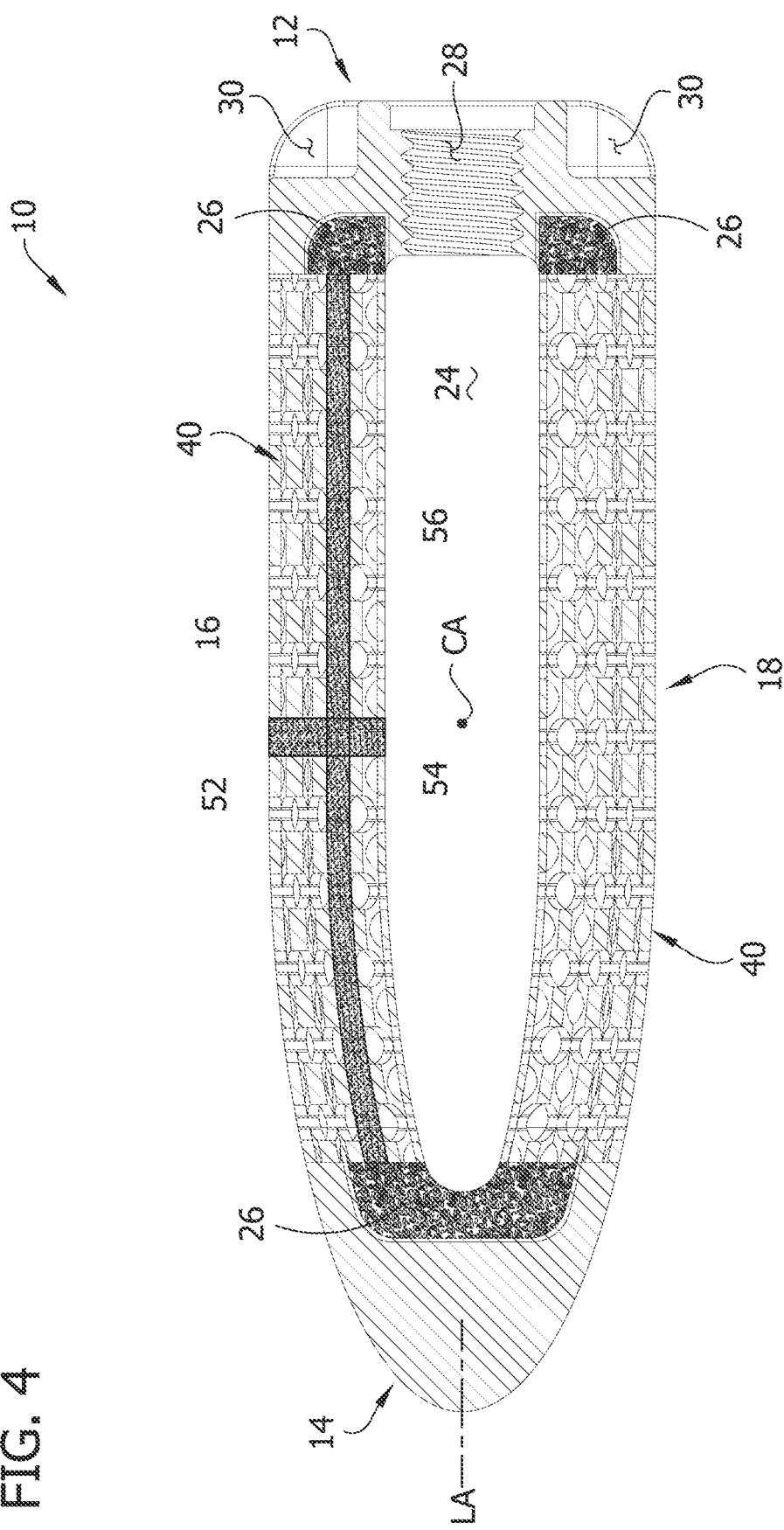
FIG. 4 is a cross section of the interbody spacer taken in the plane defined by the line 4-4 in FIG. 2.
Figure 5:
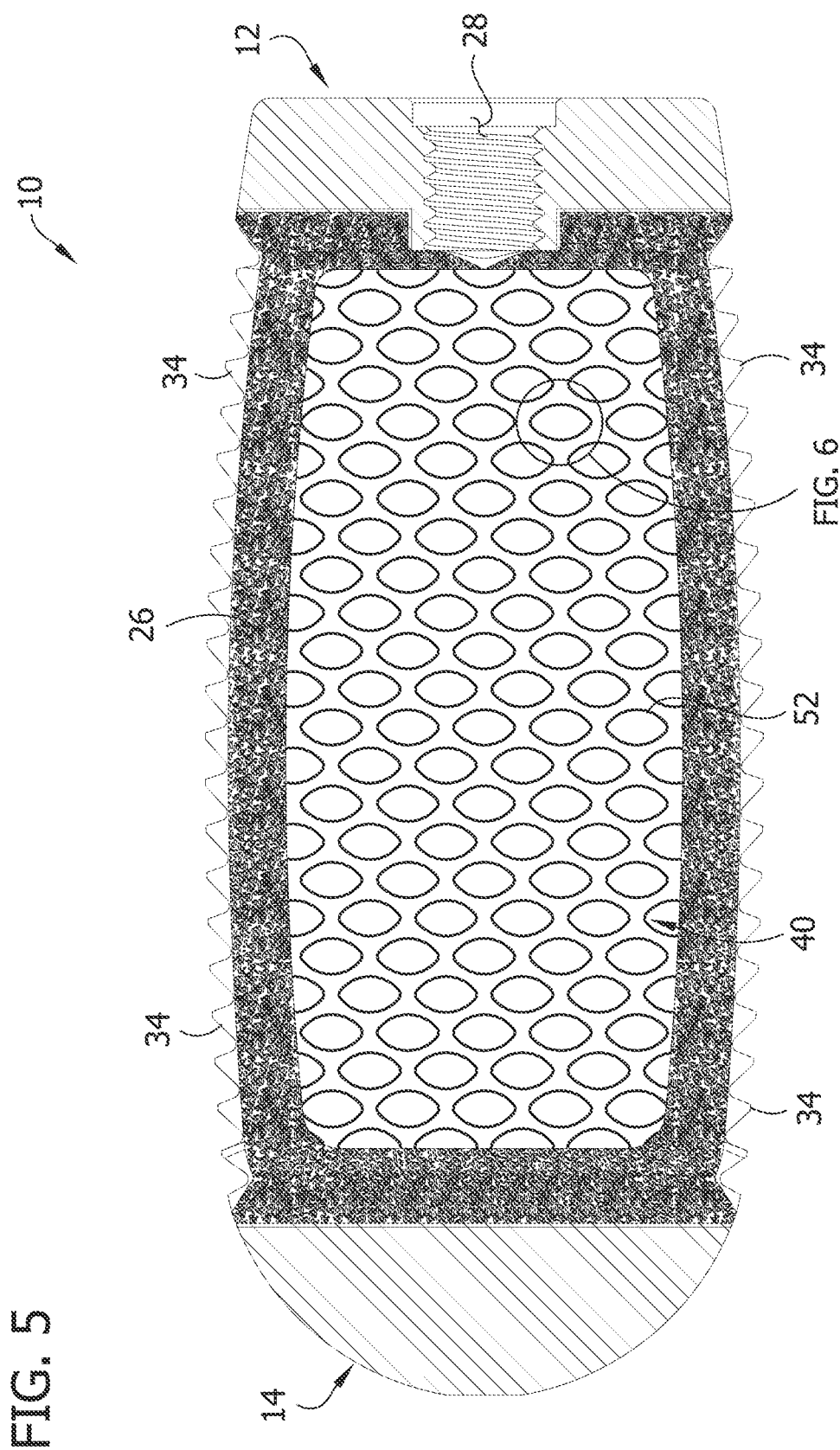
FIG. 5 is a cross section of the interbody spacer taken in the plane defined by the line 5-5 in FIG. 3.
Figure 6:
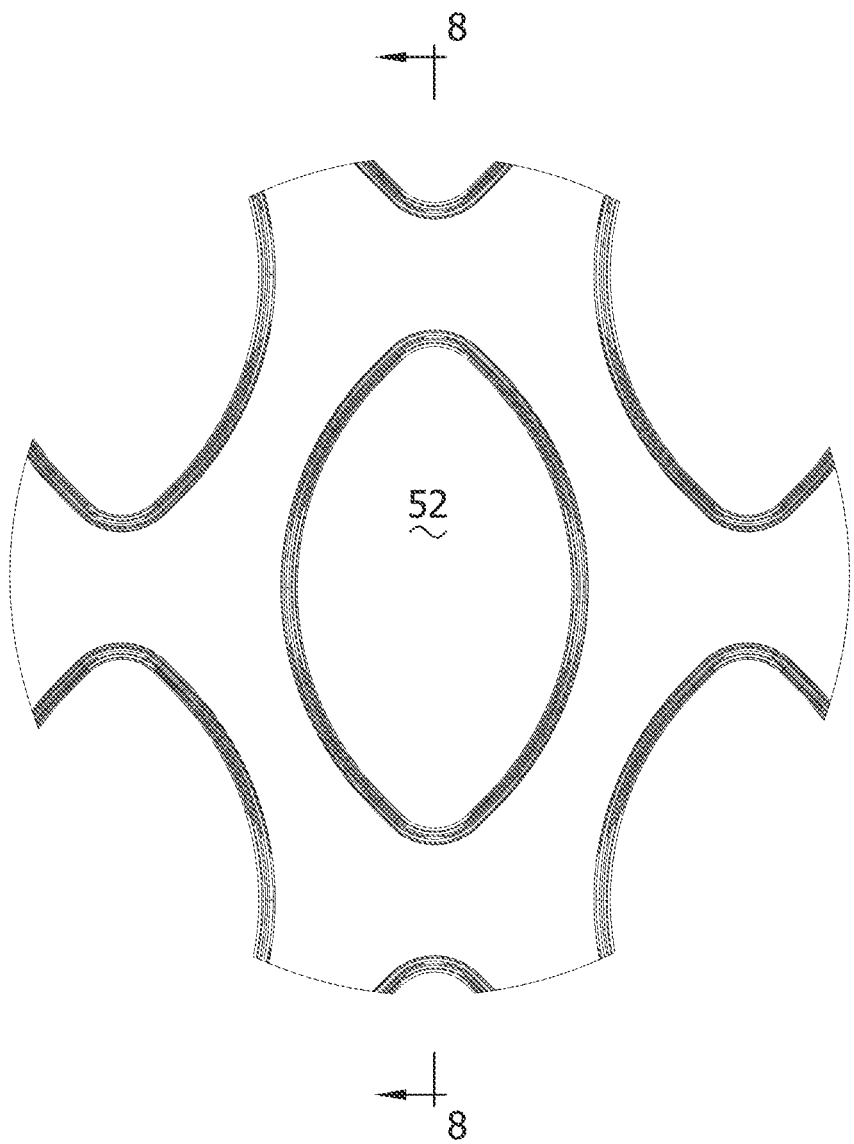
FIG. 6 is an enlarged view of transverse passages of the interbody spacer as indicated in FIG. 5.

As shown in FIGS. 1, 4 and 7, each side wall 16, 18 further includes a three-dimensional lattice (i.e., 3D lattice), generally indicated at 40, disposed heightwise between the upper and lower open-cell metal foam 26 and disposed longitudinally between the first and second longitudinal end portions 12, 14. Solid frames 42 surround outer portions of the 3D lattices 40. As shown in FIG. 7, the open-cell metal foam 26 is adjacent (e.g., secured to) and inward of the interior surface of the solid frames 42 and at least partially surrounds inner portions of the 3D lattices 40. Each 3D lattice 40 defines a plurality of intersecting passages extending therethrough: a set of transverse passages 52 extending transversely through the corresponding side wall 16, 18 from the interior cavity 24 through the exterior of the side wall; a set of heightwise passages 54 extending heightwise through the 3D lattice 40 from an upper end of the 3D lattice to a lower end of the 3D lattice; and a set of longitudinal passages 56 extending generally longitudinally through the 3D lattice from a first longitudinal end to a second longitudinal end of the 3D lattice. As can be seen and understood, the heightwise passages 54 are in direct communication with the open-cell metal foam 26 at the upper and lower faces 20, 22, and all of the passages 52, 54, 56 are in communication with and intersect one another. In this way, bone growth from vertebrae into the open-cell metal foam 26 at the upper and lower faces 20, 22 can enter the 3D lattice 40 and grow within the interconnected passages 52, 54, 56 of the 3D lattice.

In general, the open area or porosity of each 3D lattice 40 (and thus each side wall 16, 18) increases from adjacent the exterior surface of the corresponding side wall toward its interior surface of the corresponding side wall. Relatedly, the structural integrity (i.e., the compressive strength) of each 3D lattice 40 (and thus each side wall 16, 18) increases from adjacent the interior surface of the corresponding side wall toward the exterior surface of the corresponding side wall because there is less open area and more structure adjacent the exterior surface compared to the interior surface. In this way, there is more open area within each side wall 16, 18 for bone growth at a location adjacent the interior cavity 24 and there is more compressive strength to absorb compressive force adjacent the exterior surface of the interbody spacer 10.

Figure 8:
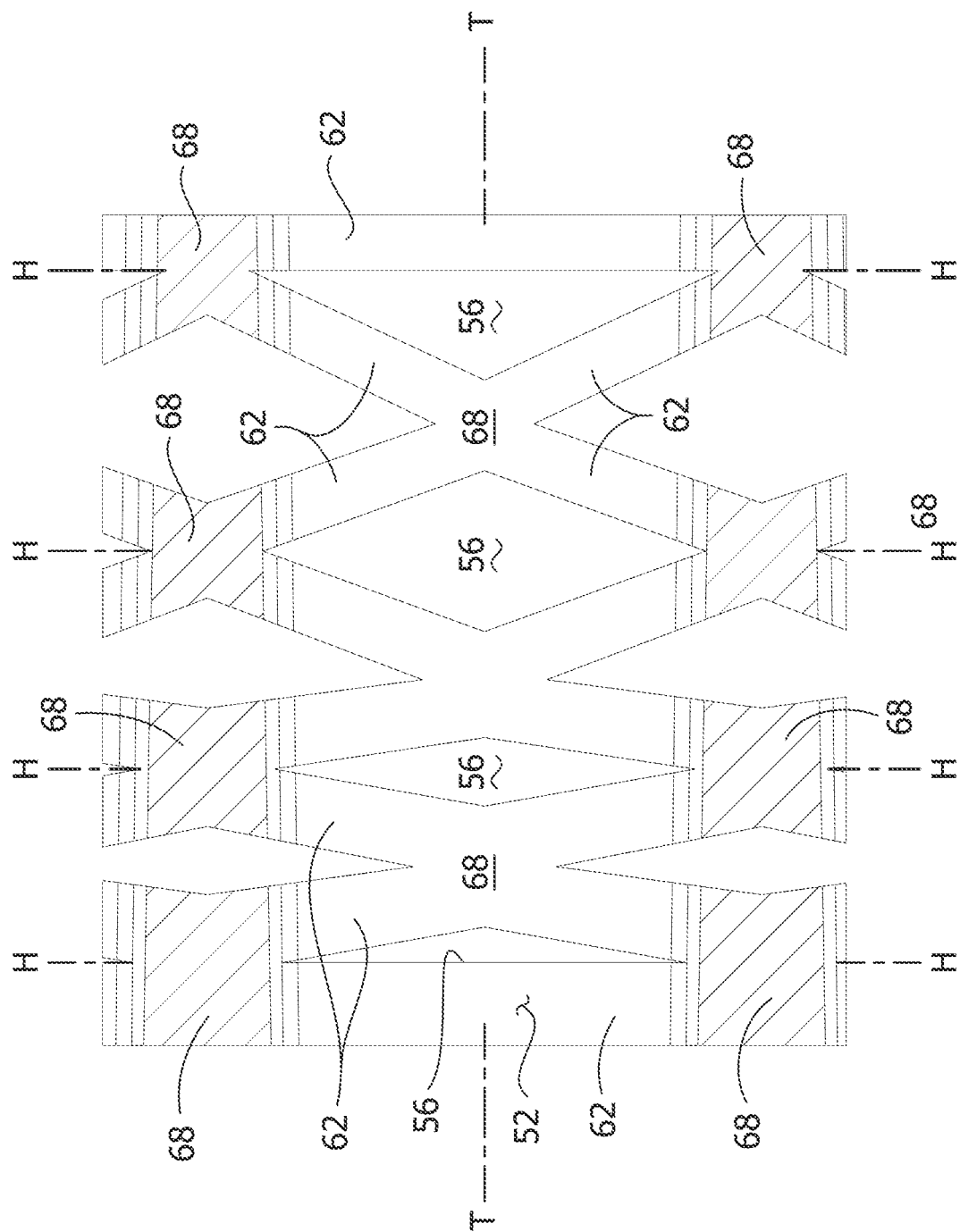
FIG. 8 is a cross section of the interbody spacer taken in the plane defined by the line 8-8 in FIG. 7.
Figure 9:
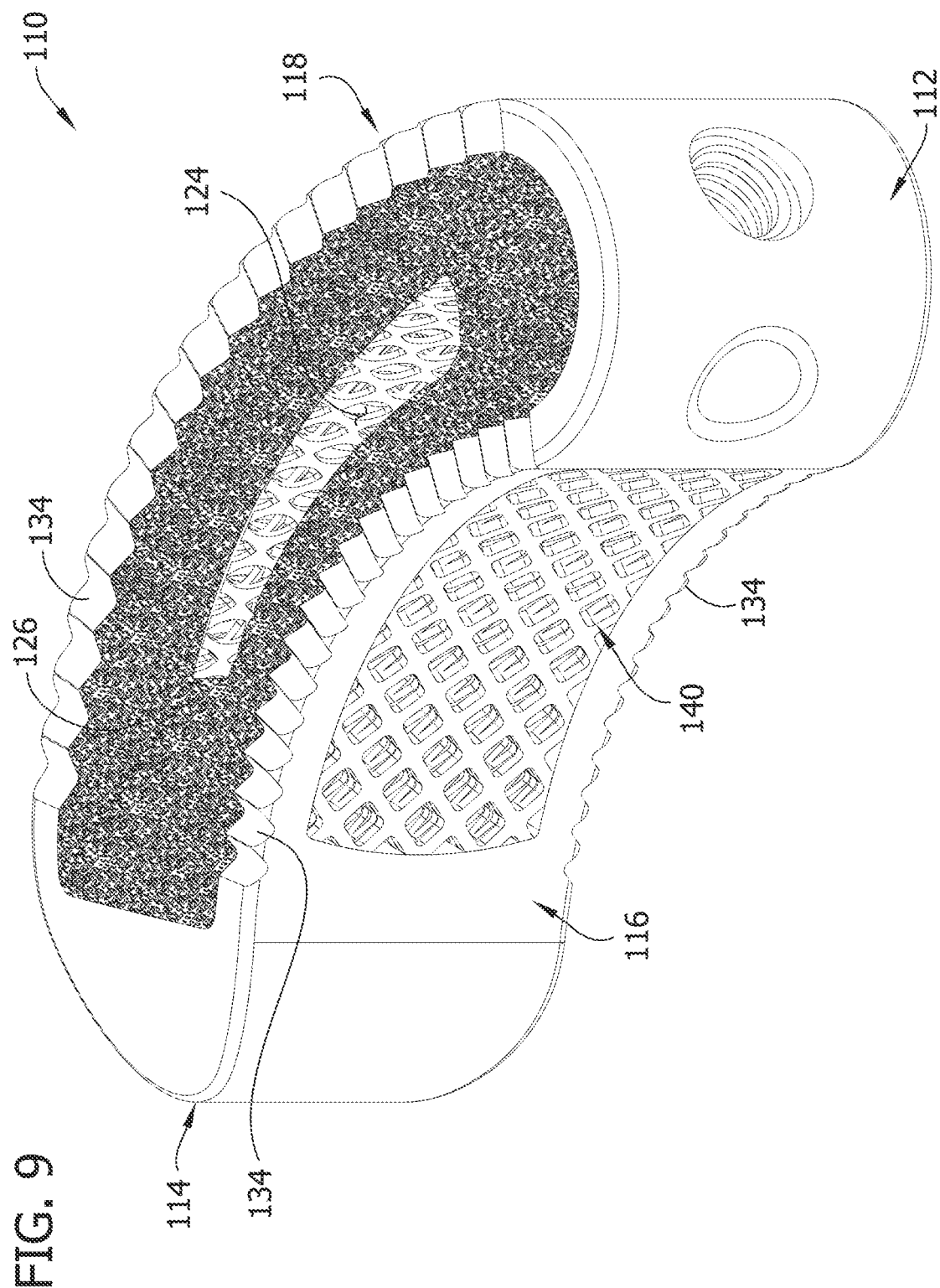
FIG. 9 is a perspective of another embodiment of an interbody spacer constructed according to the teachings of the present disclosure.
Figure 10:
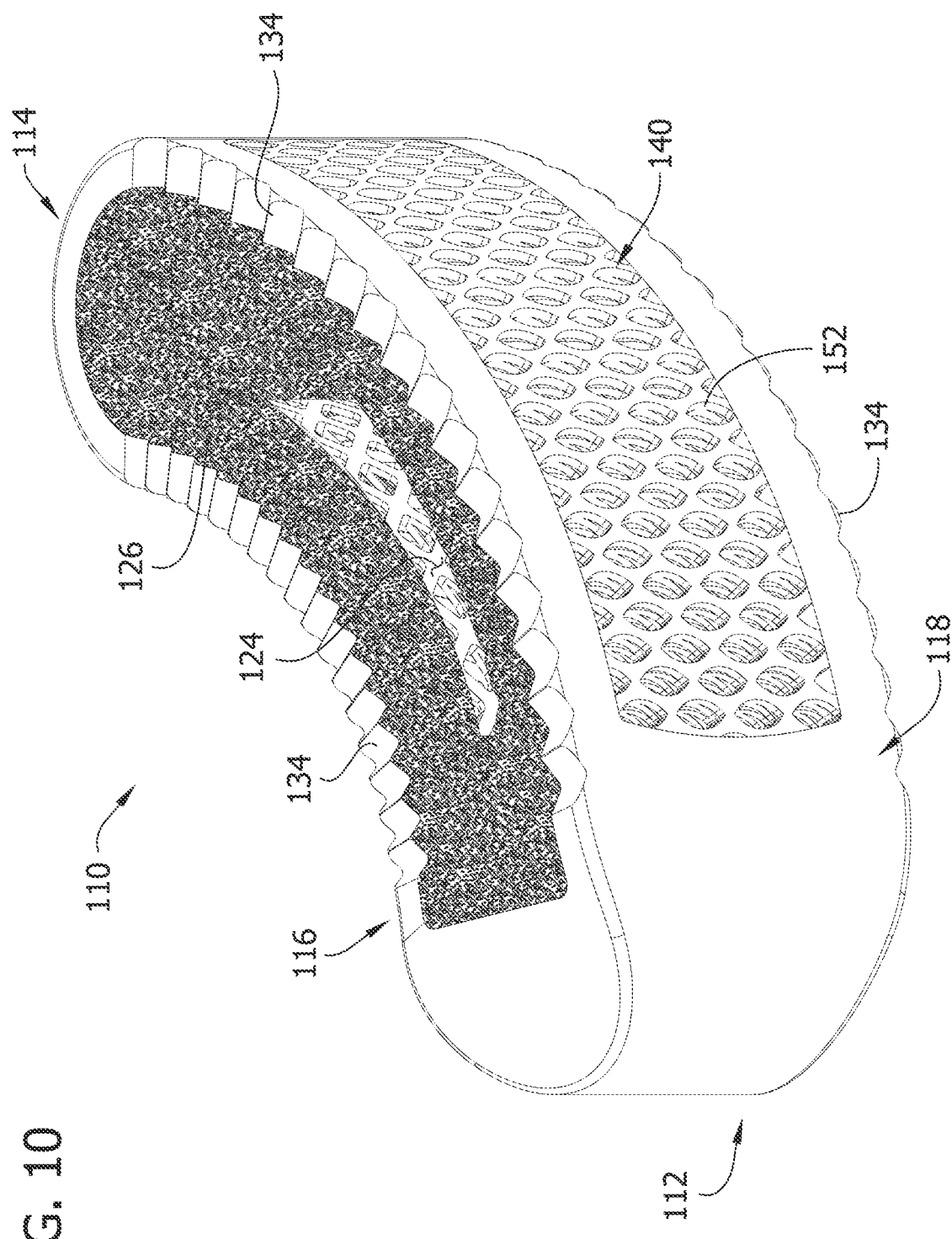
FIG. 10 is another perspective of the interbody spacer of FIG. 9.
Figure 11:
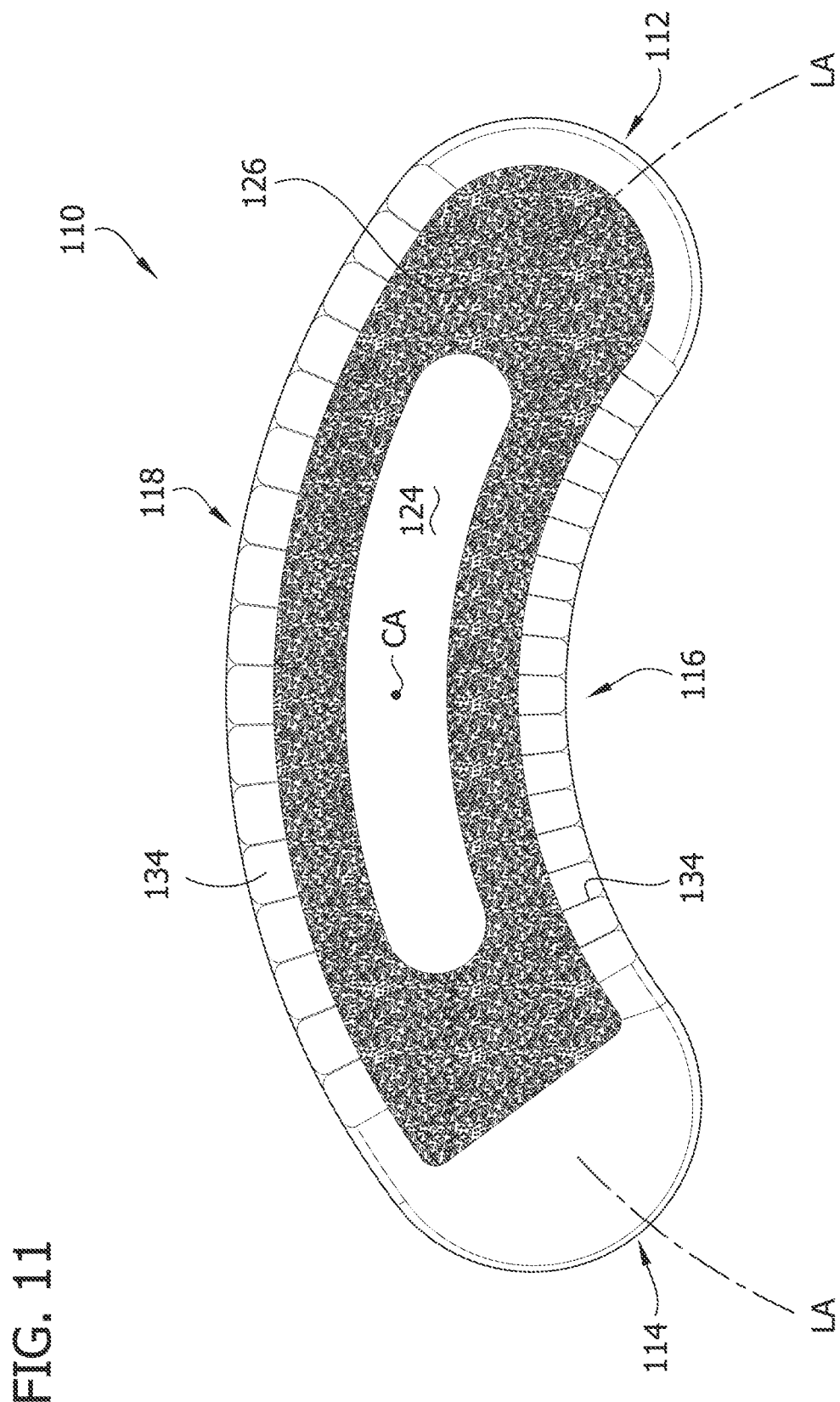
FIG. 11 is a top plan view of the interbody spacer of FIG. 9.

In the illustrated embodiment, the transverse passages 52 are arranged in longitudinal and heightwise rows extending longitudinally and heightwise of the corresponding side wall 16, 18, respectively. A single transverse passage 52 is shaded in FIG. 4 and another single transverse passage 52 is shaded in FIG. 7 for illustrative purposes. An enlarged transverse passage 52 is illustrated in FIG. 8. The transverse passages 52 may have the same cross-sectional shapes and cross-sectional dimensions (e.g., cross-sectional areas), although the transverse passages may not be uniform in shape and dimensions. In the illustrated example, each transverse passage 52 may have a generally oval or oblong cross-sectional shape, with a major axis extending heightwise and a minor axis extending longitudinally. The transverse passages 52 may have other cross-sectional shapes. The cross-sectional area of each transverse passage 52 gradually increases from the exterior surface to the interior surface such that the transverse passage generally "opens up" toward the interior surface, and tapers toward the exterior surface. In one example, the cross-sectional area of each transverse passage 52 at the exterior surface may be from about 1.0 mm² to about 2.0 mm², and the cross-sectional dimension of each transverse passage at the interior surface may be from about 1.5 mm² to about 2.5 mm². In one example, the cross-sectional area of each transverse passage 52 may increase by about 25% to about 50% from adjacent the exterior surface to adjacent the interior surface. As shown in FIG. 7, upper and lower transverse passages 52 are in communication with the open-cell metal foam 26 at the respective upper and lower faces 20, 22 to allow bone growth from the open-cell metal foam to enter the transverse passages 52 and the 3D lattice 40 in general.

In the illustrated embodiment, the heightwise passages 54 are arranged in rows extending longitudinally and transversely along the corresponding side wall 16, 18. A single heightwise passage 54 is shaded in FIG. 4 and another single heightwise passage is shaded in FIG. 7 for illustrative purposes. The heightwise passages 54 intersect each transverse passage 52 and each longitudinal passage 56 at a plurality of locations along each of the passages. In the illustrated embodiment, the passages 52, 54, 56 intersect each other at generally orthogonal angles. Each heightwise passage 54 may have a uniform cross-sectional dimension along its length. For example, as shown in FIG. 4, each heightwise passage 54 may have a generally oval or oblong cross-sectional shape, with a major axis extending longitudinally and a minor axis extending transversely. The heightwise passages 54 may have other cross-sectional shapes. As shown in FIG. 4, each heightwise passage 54 in a corresponding longitudinal row may be uniform (i.e., the same cross-sectional dimensions). As shown in FIGS. 4 and 7, the heightwise passages 54 in a corresponding transverse row may have non-uniform cross-sectional dimensions. In particular, the cross-sectional areas of the heightwise passages 54 generally increase from adjacent the exterior surface toward the interior surface so that the cross-sectional area of a first heightwise passage is greater than a cross-sectional area of a second heightwise passage that is disposed outward of the first heigthwise passage in the same transverse row. In one example, the cross-sectional areas of the heightwise passages 54 may be from about 0.1 mm² to about 0.8 mm². In one example, the cross-sectional area of the heightwise passages 54 in the same transverse row may increase by about 75% to about 85% from adjacent the exterior surface toward the interior surface.

In the illustrated embodiment, the longitudinal passages 56 are arranged in rows extending heightwise and transversely along the corresponding side wall 12, 14. A single longitudinal passage 56 is shaded in FIG. 4 and another single longitudinal passage is shaded in FIG. 7 for illustrative purposes. The longitudinal passages 56 intersect the transverse passages 52 and the heightwise passages 54 at a plurality of locations along the passages. Each longitudinal passage 56 may have a uniform cross-sectional dimension along its length. For example, each longitudinal passage 56 may have a generally diamond or rhombus cross-sectional shape, with a major axis extending heightwise and a minor axis extending transversely. The longitudinal passages 56 may have other cross-sectional shapes. In the illustrated embodiment, the longitudinal passages 56 follow the curves of the exterior and interior surfaces adjacent the bullet nose of the second longitudinal end portion 14 so that the transverse distance of each longitudinal passage relative to the interior and exterior surfaces is constant along the length of the longitudinal passage. Each longitudinal passage 56 in a corresponding heightwise row may have uniform cross-sectional shapes and dimensions (i.e., the same cross-sectional areas). The longitudinal passages 56 in a corresponding transverse row may have non-uniform cross-sectional shapes and/or dimensions (e.g., non-uniform cross-sectional areas). In particular, as shown in FIG. 7 the cross-sectional areas of the longitudinal passages 56 generally increase from adjacent the exterior surface toward the interior surface so that the cross-sectional area of a first longitudinal passage is greater than a cross-sectional area of a second longitudinal passage that is disposed outward of the first longitudinal passage in the same transverse row. In one example, the cross-sectional areas of the longitudinal passages 56 may be from about 0.4 mm² to about 1.0 mm². In one example, the cross-sectional areas of the longitudinal passages 56 in the same transverse row may increase by about 250% to about 340% from adjacent the exterior surface toward the interior surface.

In the illustrated embodiment, the 3D lattices 40 comprise interconnected structural strut members 62. The strut members 62 are connected to one another at nodes 68. In the illustrated embodiment, eight strut members 62 are connected at one node 68 (i.e., eight strut members connect to a single node). The non-randomized arrangement and configurations of the strut members 62 define the pattern of intersecting passages extending through the side walls 16, 18. In the illustrated embodiment, the strut members 62 adjacent the exterior of each side wall 16, 18 have cross-sectional dimensions (e.g., cross-sectional areas) greater than the cross-sectional dimensions (e.g., cross-sectional areas) of the strut members adjacent the interior of the corresponding side wall. As shown in FIGS. 4 and 8, the cross-sectional areas of the strut members 62 may decrease gradually toward the interior surface of the corresponding side wall 16, 18. Moreover, as also shown in FIG. 8, the strut members 62 extend from nodes 68 at increasing angles relative to a transverse axis T passing through adjacent nodes and a heightwise axis H passing through adjacent nodes from adjacent the interior surface toward the exterior surface of the walls 16, 18. The strut members 62 also extend from nodes 68 at increasing angles relative to a longitudinal axis passing through adjacent nodes from adjacent the interior surface toward the exterior surface of the walls 16, 18. In this way, the 3D lattice 40 provides more structural support (e.g., compressive strength) adjacent the exterior surface of the side walls 16, 18 compared to the interior surfaces, and the 3D lattice provides more open area adjacent the interior surface of the side walls compared to the exterior surfaces. The 3D lattice 40 may have other configurations of strut members 62.

The interbody spacer 10 may be integrally formed as a one-piece monolithic component. For example, the entirety of the interbody spacer 10 may be formed by additive manufacturing, such as by direct metal laser sintering or by electron beam melting processes, as is generally known. The interbody spacer 10 may be formed entirely from a single type of metal, such as titanium, or the interbody spacer may comprise more than one type of metal. The interbody spacer 10 may be formed in other ways.

In use, the interior cavity 24 may be packed with bone graft material and then inserted within an interbody space between two adjacent vertebrae in a suitable surgical procedure such that the upper face 20 of the spacer 10 contacts the upper or superior vertebra and the lower face of the spacer contacts the lower or inferior vertebra. In this position, the upper and lower teeth 34 anchor into the respective superior and inferior vertebrae, and the open-cell metal foam 26 at the upper and lower faces 20, 22 are in close proximity and/or are contacting the respective superior and inferior vertebrae. After insertion of the spacer 10 and completion of the surgery, it is envisioned that bone from the adjacent vertebrae will grow into the porous open-cell metal foam 26 of the first and second walls 16, 18 at the upper and lower faces 20, 22. Further in-growth into the open-cell metal foam 26 will lead the bone growth into the 3D lattices 40 of the first and second side walls 18, 20 because the open-cell metal foam is in communication with the transverse, heightwise, and longitudinal passages 52, 54, 56 of the 3D lattice 40. Further bone growth into the 3D lattice 40 will occur, particularly (it is believed) into the more open porous interior spaces of the first and second side walls 16, 18 where the 3D lattice is more porous. It is believed such enhanced bone growth into the interbody spacer 10 by way of the open-cell metal foam 26 and the porous 3D lattice 40 promotes bone growth of the vertebrae and enhances fusion of the patient's spine, as is desired in such fusion surgery.

Referring to FIGS. 9-16, another embodiment of an interbody spacer is generally indicated at reference numeral 110. This interbody spacer 110 is designed for use in transforaminal lumbar interbody fusion (TLIF) surgery, and is referred to as a TLIF interbody spacer. This TLIF interbody spacer 110 is similar structurally to the PLIF interbody spacer 10. As such, the TLIF spacer 110 has essentially the same structurally elements as the PLIF spacer 10, which are indicated by corresponding reference numerals plus 100. Differences between this TLIF interbody spacer 110 and the PLIF interbody spacer 10 are discussed below.

Figure 12:
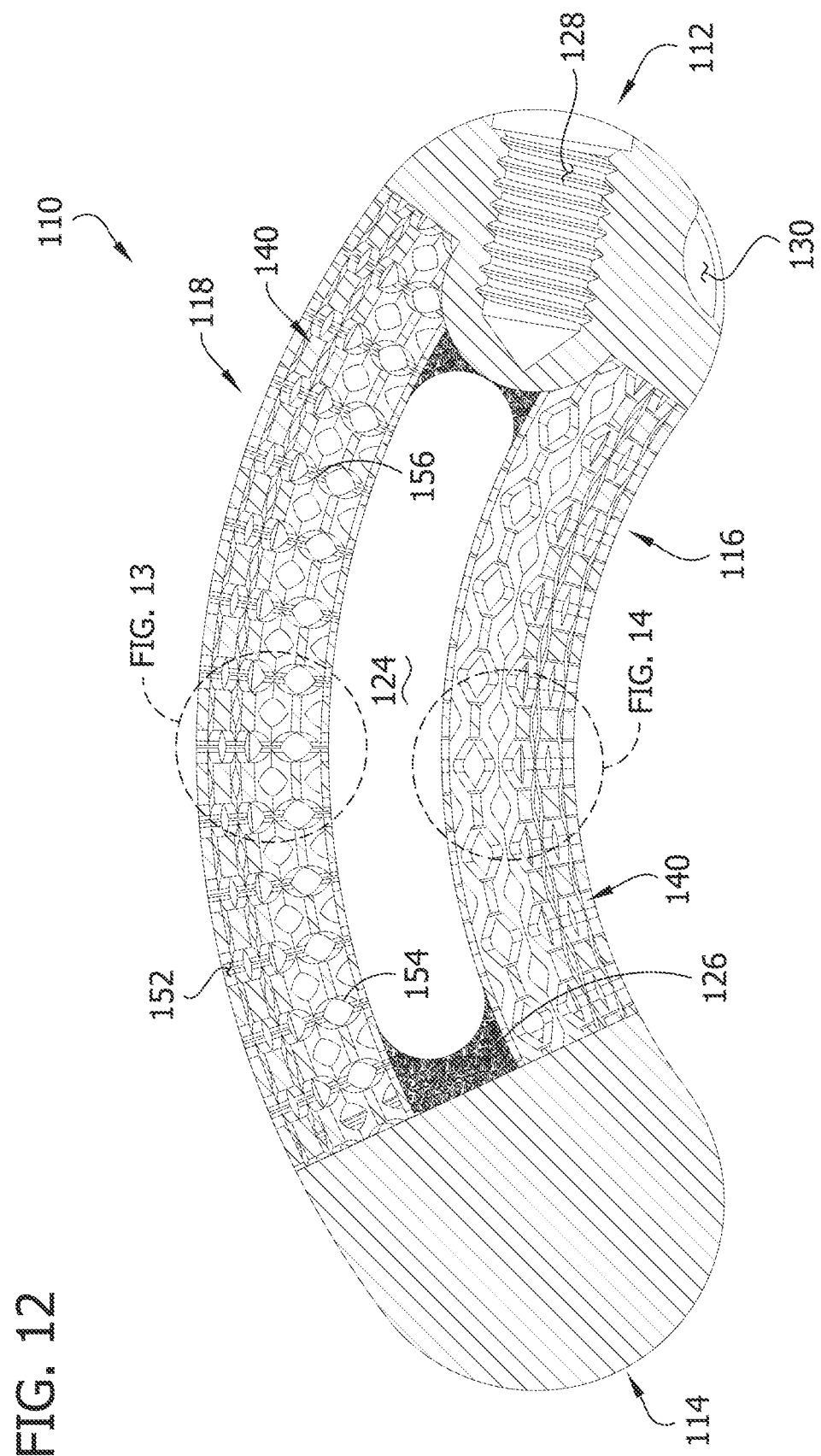
FIG. 12 is a longitudinal section of the interbody spacer of FIG. 9.
Figure 13:
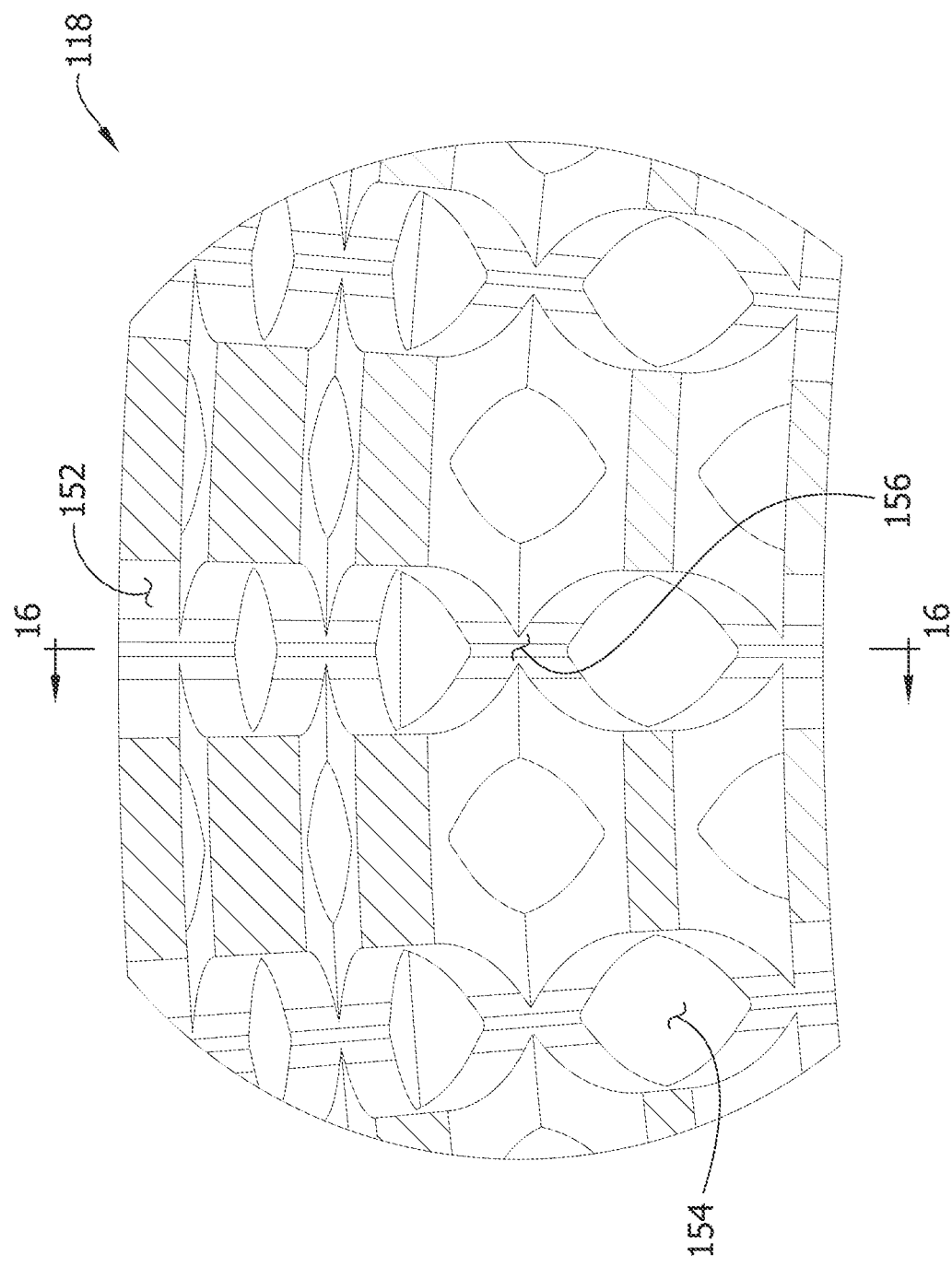
FIG. 13 is an enlarged view of the longitudinal section of FIG. 12.
Figure 14:
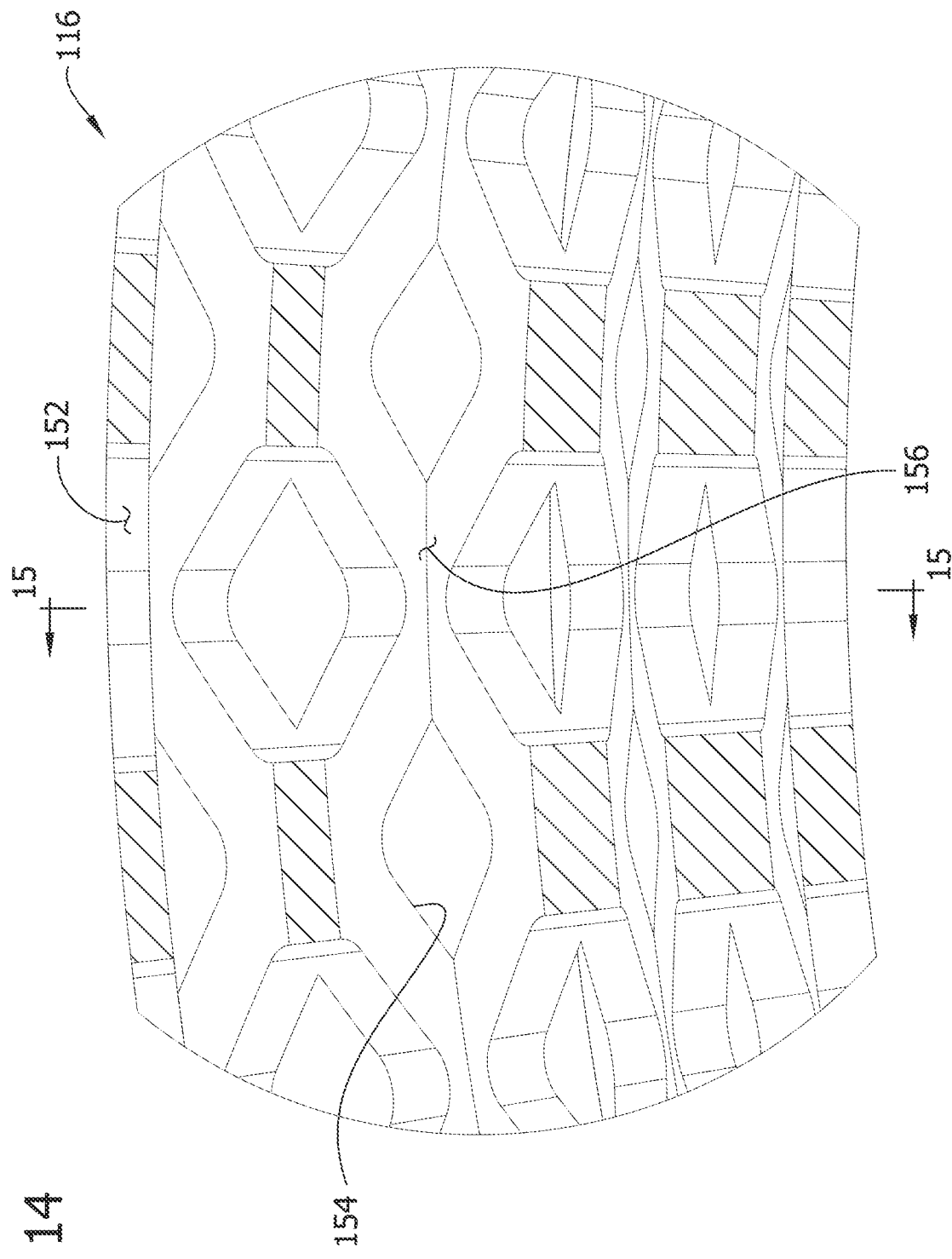
FIG. 14 is an enlarged view of the longitudinal section of FIG. 12.
Figure 15:
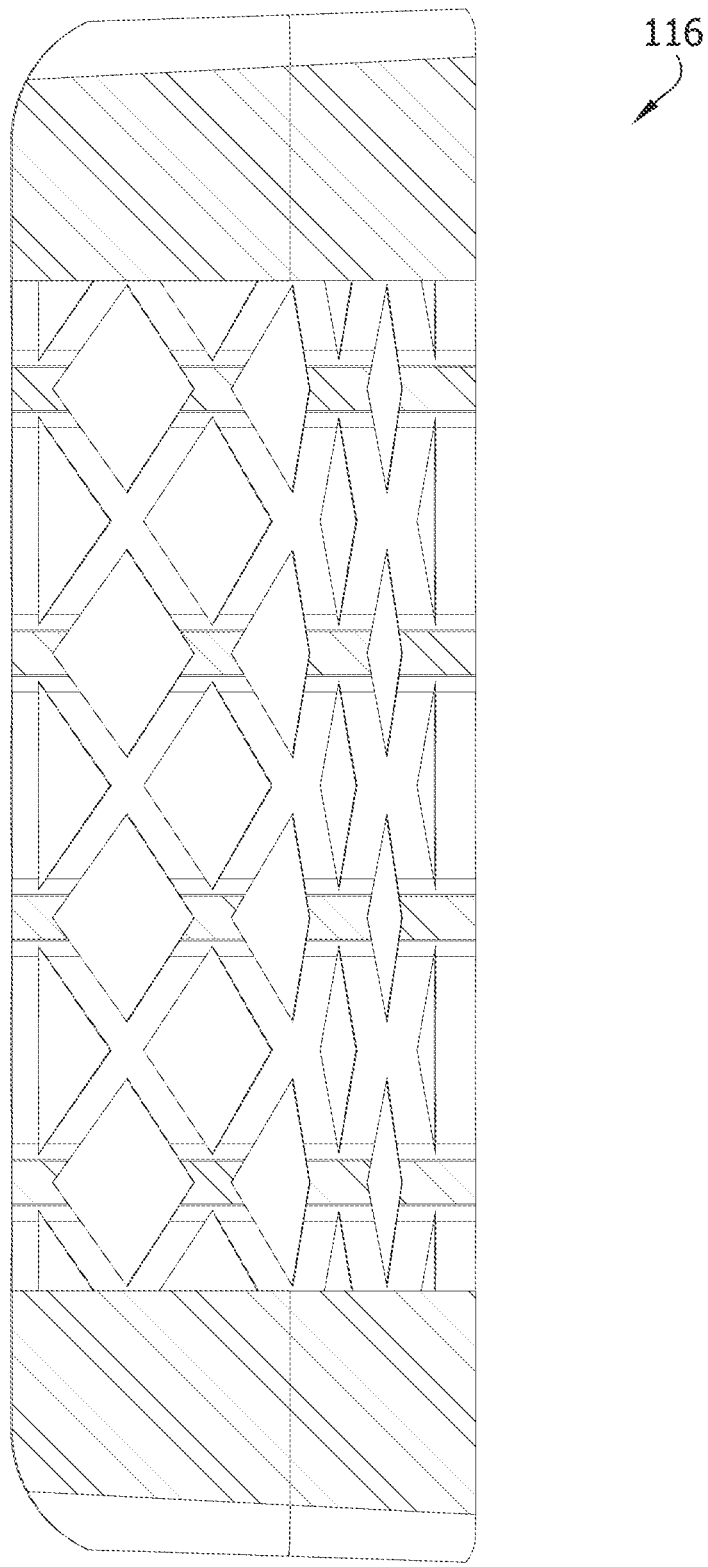
FIG. 15 is a cross section taken along the line 15-15 in FIG. 14.
Figure 16:
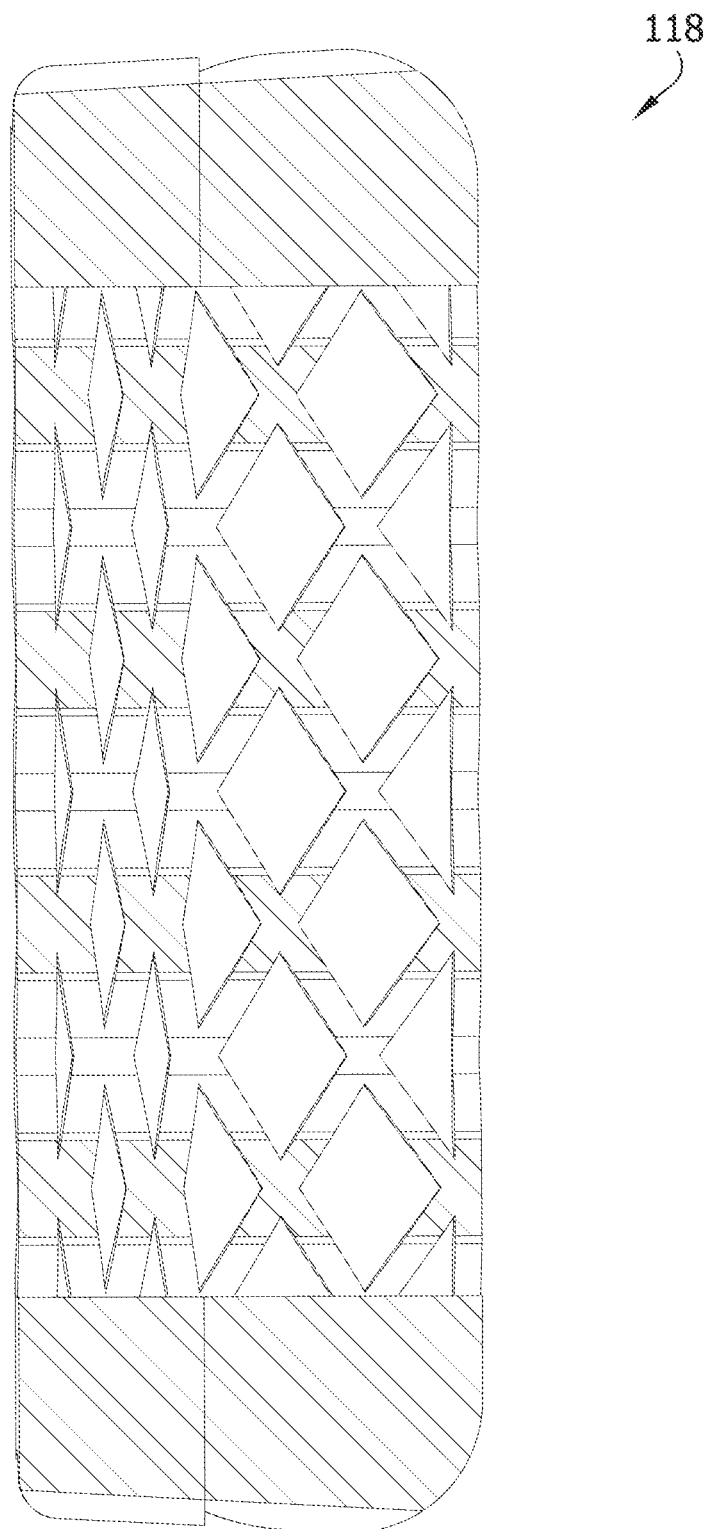
FIG. 16 is a cross section taken along the line 16-16 in FIG. 13.

One difference between this TLIF interbody spacer 110 and the PLIF interbody spacer 10 is that the TLIF interbody spacer is curved along its length, such that the first and second side walls 116, 118 have arcuate shapes along their respective lengths. The first side wall 116 has a longitudinal axis that is an inner arc compared to the longitudinal axis of the second side wall 118 such that the longitudinal axis of the first side wall has a larger radius of curvature compared to the longitudinal axis of the second side wall. As shown in FIG. 12, the longitudinal passages 156 of the first and second side walls 116, 118 follow the arcs or curves of the respective first and second side walls. Thus, the longitudinal axes of the longitudinal passages 156 are offset curves with respect to one another and with respect to the longitudinal axis of the respective first and second side walls 116, 118. Moreover, as shown in FIG. 12, the transverse passages 152 extend along radii of the imaginary circles that fit the arcs of the corresponding first and second side walls 116, 118.

Another difference between this TLIF interbody spacer 110 and the PLIF interbody spacer 10 is that one or more of the transverse, longitudinal, and heightwise passages 152, 154, 156 of the first side wall 116 have different cross-sectional shapes and/or cross-sectional sizes (e.g., cross-sectional areas) than the corresponding passages 152, 154, 156 of the second side wall 118. In particular, the cross-sectional shapes of the transverse (or radial) passages 152 of the first side wall 116 is generally diamond-shaped and have larger cross-sectional areas, while the cross-sectional shapes of the transverse (or radial) passages of the second side wall 118 is generally oval or oblong-shaped and have smaller cross-sectional areas. The differences in the transverse passages 152 and/or the other passages of the first and second walls 116, 118 is due to the fact that it is believed that the first side wall, being the radially outer side wall, will take on more of a compressive load when properly positioned in the interbody space 110. Thus, the first side wall 116 is designed to provide more structural support (e.g., have more compressive strength) than the second side wall 118. Relatedly, the second side wall 118 will be more porous and have more percentage of open area than the first side wall 116.

Yet another difference between this TLIF interbody spacer 110 and the PLIF interbody spacer 10 is that the row of teeth 134 on the first side wall 116 (the radially outer side wall) are smoother or more blunt (i.e., the edges of the teeth are less sharp or pointed) than the row of teeth on the second side wall 118. The outer radius of the teeth 134 on the first side wall 116 is also more rounded and less sharp than the outer radius of the teeth on the second side wall 118. These features facilitate insertion of the TLIF interbody spacer 110 during the TLIF procedure. The teeth 134 on the first side wall 116 is more likely to come into contact with tissue (e.g., a nerve) during insertion, and therefore, by smoothing the teeth it is less likely that the teeth with puncture, cut and/or tear tissue during insertion.

The TLIF interbody spacer 110 may be integrally formed as a one-piece monolithic component. For example, the entirety of the interbody spacer 110 may be formed by additive manufacturing, such as by direct metal laser sintering or by electron beam melting processes, as is generally known. The interbody spacer 110 may be formed entirely from a single type of metal, such as titanium, or the interbody spacer may comprise more than one type of metal. The interbody spacer 110 may be formed in other ways.

In use, the TLIF interbody spacer 110 may be implanted in the patient in a suitable manner. It is believed the TLIF interbody spacer 110 promotes bone ingrowth in the same manner as described above with respect to the PLIF interbody spacer 10.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An implant for a surgical procedure comprising:
   an implant body configured to be implanted in a subject; and
   open-cell metal foam on the implant body, wherein the open-cell metal foam is configured to enable bone of the subject to grow into the open-cell metal foam;
   wherein the implant body comprises a longitudinal end comprising at least a tool-receiving opening or a tool-receiving groove.

2. The implant set forth in claim 1, wherein the implant body defines a recessed portion, wherein the open-cell metal foam is disposed in the recessed portion of the implant body.

3. The implant set forth in claim 2, wherein the open-cell metal foam defines a portion of an exterior surface of the implant.

4. The implant set forth in claim 2, wherein the recessed portion comprises a plurality of recessed portions.

5. The implant set forth in claim 2, wherein the implant consists essentially of titanium.

6. The implant set forth in claim 2, wherein the implant consists of titanium.

7. The implant set forth in claim 2, wherein the implant is formed as a one-piece, monolithic component.

8. The implant set forth in claim 7, wherein the implant is formed by additive manufacturing.

9. A method of making an implant for a surgical procedure, the method comprising:
- forming an implant body, the implant body configured to be implanted in a bone of a subject; and
- forming open-cell metal foam on the implant body, wherein the open-cell metal foam is configured to enable the bone to grow into the open-cell metal foam,
- wherein said forming an implant body and said forming open-cell metal foam comprises additively manufacturing the implant body and the open-cell metal foam as a one-piece, monolithic component;
- wherein the implant body comprises a longitudinal end comprising at least a tool-receiving opening or a tool-receiving groove.

10. The method of making an implant set forth in claim 9, wherein said forming an implant body comprises forming a recessed portion, wherein said forming open-cell metal foam comprises forming the open-cell metal foam in the recessed portion.

11. The method of making an implant set forth in claim 10, wherein said additively manufacturing the implant body and the open-cell metal foam comprises additively manufacturing the implant using titanium.

12. A surgical method comprising:
- inserting an implant into bone of a subject, the implant comprising an implant body and open-cell metal foam on the implant body; and
- enabling bone growth into the open-cell metal foam;
- wherein the implant body comprises a longitudinal end comprising at least a tool-receiving opening or a tool-receiving groove.

13. The implant set forth in claim 2, wherein the implant body is designed and constructed to be load-bearing.

* * * * *